United States Patent
Heydenreich et al.

(12)

(10) Patent No.: US 6,723,885 B1
(45) Date of Patent: Apr. 20, 2004

(54) BISPHENOL PRODUCTION

(75) Inventors: Frieder Heydenreich, Düsseldorf (DE); Michael Prein, Brasschaat (BE); Michael Bödiger, League City, TX (US); Rainer Neumann, Krefeld (DE); Gerhard Fennhoff, Willich (DE); Johan Vaes, Kalmthout (BE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/129,757

(22) PCT Filed: Oct. 30, 2000

(86) PCT No.: PCT/EP00/10655

§ 371 (c)(1),
(2), (4) Date: Aug. 26, 2002

(87) PCT Pub. No.: WO01/34544

PCT Pub. Date: May 17, 2001

(30) Foreign Application Priority Data

Nov. 11, 1999 (DE) .......................................... 199 54 311

(51) Int. Cl.⁷ .............................................. C07C 39/16
(52) U.S. Cl. ........................................ 568/728; 422/140
(58) Field of Search ........................... 568/728; 422/140

(56) References Cited

U.S. PATENT DOCUMENTS

| 4,327,229 | A | * | 4/1982 | Mendiratta |
| 5,475,152 | A | * | 12/1995 | Kissinger |
| 5,723,689 | A | | 3/1998 | Pressman et al. ........... 568/724 |
| 5,785,823 | A | * | 7/1998 | Meurer |
| 5,786,522 | A | | 7/1998 | Cipullo ...................... 568/724 |

FOREIGN PATENT DOCUMENTS

EP 0 758 637 2/1997

* cited by examiner

*Primary Examiner*—Michael L. Shippen
(74) *Attorney, Agent, or Firm*—Joseph C. Gil; James R. Franks

(57) ABSTRACT

A process for the production of 2,2-bis(4-hydroxyphenyl) propane (BPA) is disclosed. The process that entails reacting acetone with phenol in the presence of cross-linked sulfonated polystyrene resins is characterised in that BPA is separated from the reaction solution downstream of the reaction unit by means of a multi-stage vacuum distillation and a subsequent single- or multi-stage layer crystallisation. The by-product stream with accumulated by-products is returned downstream of the reaction unit.

12 Claims, 1 Drawing Sheet

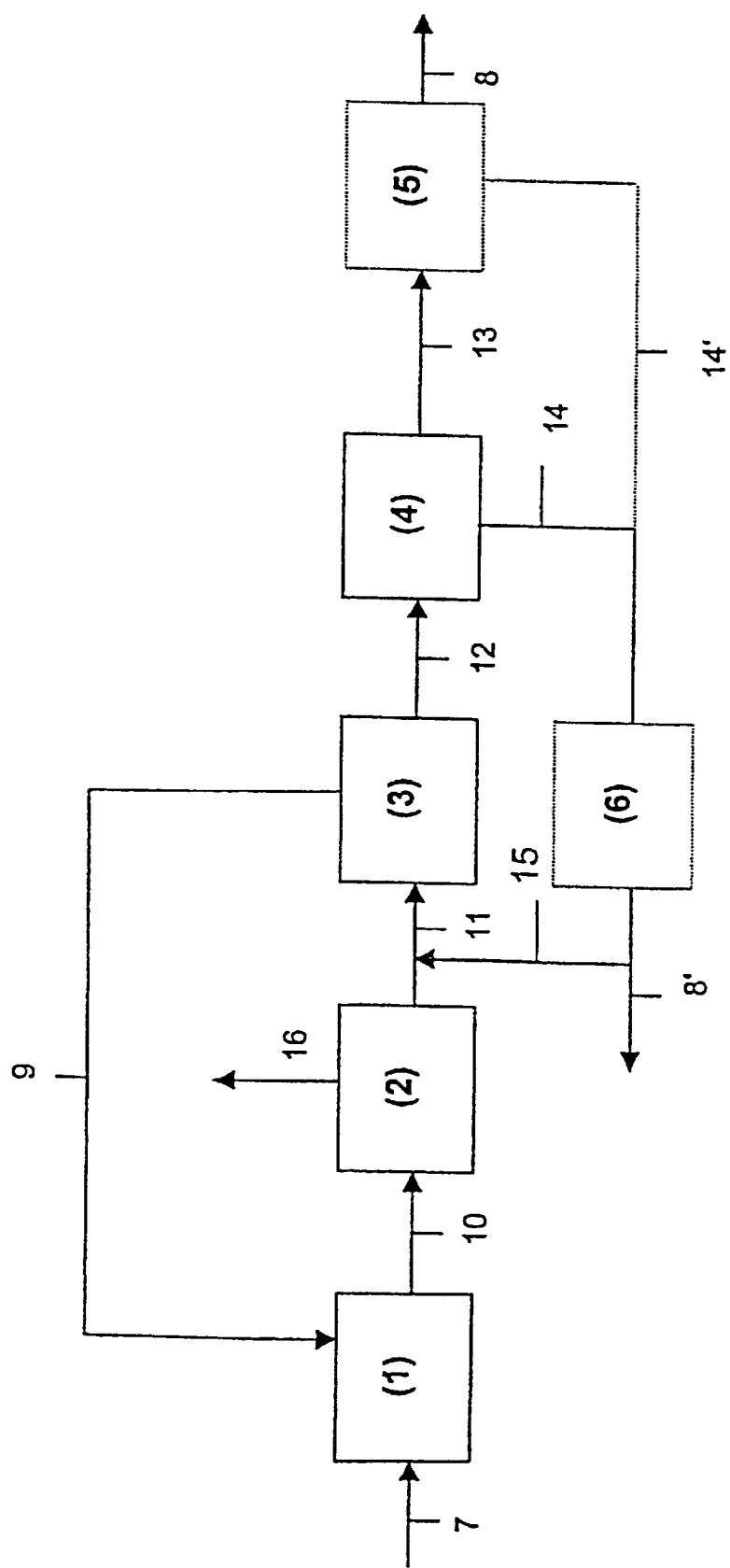

BISPHENOL PRODUCTION

BISPHENOL PRODUCTION

The invention concerns a process for the efficient production of highly pure bisphenols.

Bisphenols are important raw materials for the manufacture of polymers such as epoxy resins and particularly polycarbonates. High standards are set for the purity of bisphenols for use in this application, such that particular importance is attached to the reprocessing stages as well as to the achievement of high yields and selectivities in economic industrial-scale production processes.

According to essentially known processes, bisphenols are produced by the condensation of carbonyl compounds with aromatic alcohols in the presence of acid catalysts. A process for the technically important production of 2,2-bis(4-hydroxyphenyl)propane (BPA) comprises the reaction of acetone and phenol in the presence of cross-linked sulfonated polystyrene resins (ion exchanger resins). A phenol/acetone ratio of at least 5:1 is used here. Co-catalysts are used to obtain high selectivities; these are either dissolved homogeneously into the reactants or are fixed to the ion exchanger resin by means of covalent or ionic bonds.

The object is to separate from BPA by appropriate means the by-products that are generated in the above process for the production of BPA and to remove all residues of excess phenol from the product. The side streams generated by these measures should further be recycled in the overall process by economic means.

As a means of achieving these objects, the isolation of BPA-phenol adduct crystals from the reaction solution by suspension crystallisation with or without prior distillation is described in the literature (EP-A-829464), whereby the highly phenolic parent liquor produced during filtration of the adduct crystals, optionally after inclusion of a rearrangement reaction, is returned upstream of the reaction unit and supplemented with fresh phenol and acetone. The disadvantage of this procedure lies in the generation of large recycle streams in the process and the contamination of the catalyst bed by the return of the highly contaminated parent liquor stream.

In order to circumvent this problem, methods have been proposed that avoid the need for adduct crystallisation with the associated generation of a parent liquor circuit. EP-A-758637 describes the production of BPA by reprocessing the reaction stream in a cascade of purification stages by means of distillation, whereby the reaction stream is purified without generating back flows of acetone, water, phenol and by-products. The disadvantages of this process are the exposure of the product to high temperatures during distillation, the high energy costs involved in the distillation cascade and the substantial raw material loss resulting from dispensing with the rearrangement and recycling of the minor constituents.

In EP-A-785181 the reaction solution is likewise reprocessed without adduct crystallisation by means of vacuum distillation to remove acetone, water, phenol and optionally minor constituents, followed by melt crystallisation. In this process too, raw material losses have to be accepted as a consequence of dispensing with the recycling of BPA-containing by-product streams generated during purification.

The process according to the invention for the production and reprocessing of BPA circumvents the disadvantages described above in that the reaction mixture is purified by means of vacuum distillation, following which it undergoes layer crystallisation and the by-product streams are recycled. Highly pure BPA can be produced with the process according to the invention. The return of the by-product stream downstream of the production unit ensures that the catalyst in the reaction unit is not contaminated by recycled by-products.

The present invention thus provides a process for the production of 2,2-bis(4-hydroxyphenyl)propane (BPA) by reaction of acetone and phenol in the presence of cross-linked sulfonated polystyrene resins (ion exchanger resins), characterised in that BPA is separated from the reaction solution downstream of the reaction unit
a) by means of a multi-stage vacuum distillation and
b) a subsequent single- or multi-stage layer crystallisation,
c) and the by-product stream with accumulated by-products is returned downstream of the reaction unit.

The process according to the invention is illustrated in greater detail in the process diagram FIG. 1.

(1) represents a reaction unit in which phenol, acetone with a phenol/acetone ratio of at least 5:1, preferably at least 10:1, are added at a temperature of 40 to 110° C., preferably 45 to 70° C., to an ion exchanger catalyst system consisting of a sulfonated cross-linked polystyrene.

The ion exchanger catalyst system is preferably modified with either a covalently or ionically bonded mercapto compound.

The reaction unit may be and is preferably a layered bed or fluidised bed, with upflow or downflow operation, or a column of the reactive distillation column type.

The reaction stream (reaction solution) leaving the reaction unit (1) contains unreacted phenol and acetone, together with water, BPA and the minor constituents typically generated during the reaction, such as o,p-BPA, indanes, chromanes and more highly condensed reaction products with three or more aromatic nuclei.

The reaction is conducted such that the reaction mixture leaving the reaction unit (1) displays 70 to 95 wt. %, preferably 75 to 90 wt. % phenol; 0 to 4 wt. %, preferably 0.1 to 1.0 wt. % acetone; 0.1 to 4 wt. %, preferably 0.5 to 2.0 wt. % water; 5 to 30 wt. %, preferably 10 to 25 wt. % p,p-BPA and 0 to 3 wt. %, preferably 0.1 to 1.5 wt. % by-products.

This reaction stream is fed to a cascade of two distillation columns (2) and (3). In distillation column (2) water and acetone are removed from the reaction stream to leave a residual content of no more than 0.1 wt. % respectively.

In the second distillation column (3) phenol is then separated off to leave a residual content of no more than 25 wt. %, preferably no more than 10 wt. %, particularly preferably no more than 5%. The separated phenol is preferably returned to the reaction unit (1).

The remaining reaction stream containing minor constituents and residual phenol in addition to BPA is fed to a crystallisation unit (4). In the crystallisation unit (4) crystallisation is performed as layer crystallisation on cooled surfaces in a melt crystallisation apparatus, with continuous or batchwise operation, at temperatures of 125 to 160° C., preferably 140 to 160° C. The crystallisation may be performed as a static process or in the form of a falling-film crystallisation.

This procedure concentrates BPA and depletes the by-products and phenol. The content of phenol and of by-products was reduced in the crystallisation unit (4) by around 80% in each case as compared with the quantities present prior to entering the crystallisation unit (4).

On completion of crystal growth, the BPA crystals formed are isolated by draining off the liquid parent liquor. This is optionally followed by a further purification of the crystals, possibly and preferably by passing them through a temperature gradient by sweating. The crystals are then liquefied by raising the temperature above the melting point and drained into a collecting tank for further processing.

The BPA obtained after the crystallisation unit (4) can optionally be freed from any remaining phenol and/or minor constituents in a second unit (5). The unit (5) is preferably operated in the same way as the crystallisation unit (4). Purification may also be performed by distillation and/or desorption, however.

The by-product stream obtained in the crystallisation unit (4) and optionally (5), containing BPA, phenol and concentrated minor constituents, is returned upstream of the second distillation column (3), whereby part of the (by-)product (BPA resin) can be removed from the system to prevent an accumulation of minor constituents in the circuit.

Before being fed into the distillation column (3), the by-product stream is preferably passed through a rearrangement reactor (6), which is filled with acid ion exchangers, preferably with cross-linked sulfonated polystyrene resins, particularly with covalently or ionically bonded mercapto compounds, particularly cross-linked sulfonated polyester resins modified with 2-mercaptoethylamine (cysteamine) and operated at temperatures of 50 to 110° C., preferably 60 to 80° C. Some of the by-products contained in the by-product stream (o,p-BPA, higher condensates) are rearranged in the rearrangement reactor (6) to p,p-BPA. This increases the overall yield of BPA and reduces the content of BPA resin.

The process diagram FIG. 1 further illustrates the following components:
(7) supply unit for phenol and acetone
(8) and (8') product extraction unit
(9) phenol return line
(10) to (13) reaction stream lines
(14) and (14') by-product stream lines
(15) by-product stream or rearrangement product stream line
(16) water and acetone drainage line In the process according to the invention, high-grade BPA is obtained by economic means with minimised back flow, energy input and substance losses, without contaminating and deactivating the catalyst in the reaction unit (1) with recycled by-products. The use of rotary filters and centrifuges to separate the adduct crystals that would otherwise be formed during a suspension crystallisation of BPA is further avoided by the use of layer crystallisation. In this way the technically complex, high-maintenance operation of process equipment is avoided and the availability of the system enhanced. By virtue of its high purity and good colour index, the BPA produced in this way is particularly suitable for use as a raw material for polymers such as polycarbonates and epoxy resins in particular.

The following examples are intended to illustrate the invention. The invention is not limited to these examples. Percentage figures given below represent percentages by weight.

EXAMPLES

Example 1
Production of the Reaction Solution 4 l phenol-wetted sulfonated polystyrene resin (Lewatit SC 104, Bayer AG, covered with 5% cysteanine) is passed through a sintered glass filter into a double-walled glass reactor (5 l). The apparatus is thermostated to 70° C. and rendered inert by being evacuated and aerated with nitrogen five times. Under a nitrogen fog a solution of 96% phenol and 4.0% acetone is fed continuously into the reactor from above at 70° C. and at a flow rate of 1.5 l/h. At the reactor outlet a solution having the following composition is obtained in continuous operation: phenol 84.5%, acetone 0.3%, water 1.4%, p,p-BPA 12.7%, by-products 1.1%.

Example 2
Removal of Acetone/water From the Reaction Solution

The reaction solution (10 l) obtained in example 1 is distilled through two plate columns with 10 separation stages under a nitrogen fog. Distillation takes place at 150 mbar and a plate temperature of 130° C. A distillate with the following composition is obtained:

acetone 17.0%, water 79.3%, phenol 3.6%, others <0.1%

The bottom product displays the following composition: phenol 85.9%, p,p-BPA 12.9%, by-products 1.2%

Example 3
Removal of Phenol From the Dewatered Solution

Phenolic distillation of the solution obtained in example 2 took place in a packed column at 100 mbar; the overhead temperature was 120° C. The distillate contains >99.9% phenol and the bottom product displays the following composition: phenol 4.0%, p,p-BPA 88.3%, minor constituents 7.7%.

Example 4
Layer Crystallisation

The solution obtained in example 3 undergoes a static layer crystallisation in a melt crystallisation plant at 148 to 153° C. After crystal growth, draining off the parent liquor, washing the crystals with reaction solution and sweating off the crystals, the product crystals are melted at 165° C. and drained off. A product of the following composition is obtained: phenol: 0.7%, p,p-BPA 98.2%, by-products 1.1%.

The product stream thus obtained undergoes a second layer crystallisation conducted at a temperature of 153–156° C. After crystal growth, draining off the parent liquor, washing the crystals with reaction solution and sweating off the crystals, the product crystals are melted at 165° C. and drained off. A product of the following composition is obtained: phenol: 0.1%, p,p-BPA 99.7%, by-products 0.2%.

The accumulation of phenol and by-products in the two stages is calculated as follows:
Layer Crystallisation 1:
Phenol Reduction by 83%, By-products Reduction by 86%
Layer Crystallisation 2:
Phenol Reduction by 86%, By-products Reduction by 82%

The total amount of recycled parent liquor after the two crystallisation stages was 18% of the reaction solution used.

What is claimed is:

1. A process of preparing 2,2-bis-(4-hydroxyphenyl) propane comprising:
   (a) providing an apparatus comprising in sequence,
      (i) a reaction unit containing cross-linked sulfonated polystyrene resins,
      (ii) a first distillation column that is downstream from and in fluid communication with said reaction unit,
      (iii) a second distillation column that is downstream from and in fluid communication with said first distillation column, and
      (iv) a crystallization unit that is downstream from and in fluid communication with said second distillation column, said crystallization unit comprising a by-product conduit that is in fluid communication with said second distillation column;

(b) introducing and reacting phenol and acetone into and within said reaction unit, thereby forming a reaction unit product stream comprising 2,2-bis-(4-hydroxyphenyl)propane, phenol, acetone and by-products;

(c) introducing the reaction unit product stream into said first distillation column, thereby forming a first distillation column product stream comprising 2,2-bis-(4-hydroxyphenyl)propane;

(d) introducing the first distillation column product stream into said second distillation column, thereby forming a second distillation column product stream comprising 2,2-bis-(4-hydroxyphenyl)propane;

(e) introducing the second distillation column product stream into said crystallization unit, thereby forming a crystallization unit product stream comprising purified 2,2-bis-(4-hydroxyphenyl)propane, and a by-product stream comprising by-products; and (f) introducing at least a portion of the by-product stream from said crystallization unit into said second distillation column by means of said by-product conduit.

2. The process of claim 1 wherein said apparatus further comprises a rearrangement reactor filled with cross-linked sulfonated polystyrene resin, said rearrangement reactor being in fluid communication with said crystallization unit and said second distillation column by means of said by-product conduit, said process further comprising passing the by-product stream through said rearrangement reactor prior to introducing the by-product stream into said second distillation column.

3. The process of claim 1 wherein the cross-linked sulfonated polystyrene resin in said reaction unit is modified with a covalently or ionically bonded mercapto compound.

4. The process of claim 3 wherein the ionically bonded mercapto compound is 2-mercaptoethylamine.

5. The process of claim 1 wherein said apparatus further comprises a second crystallization unit that is downstream from and in fluid communication with said crystallization unit, said second crystallization unit comprising a second by-product conduit that is in fluid communication with the by-product conduit of said crystallization unit, said process further comprising, introducing the crystallization unit product stream into said second crystallization unit, thereby forming a second crystallization unit product stream comprising further purified 2,2-bis-(4-hydroxyphenyl)propane, and a second by-product stream comprising by-products, combining the second by-product stream with the by-product stream to form a combined by-product stream, and introducing the combined by-product stream into said distillation column.

6. The process of claim 5 wherein said apparatus further comprises a rearrangement reactor filled with cross-linked sulfonated polystyrene resin, said rearrangement reactor being in fluid communication with said crystallization unit, said second crystallization unit and said second distillation column by means of said by-product conduit and said second by-product conduit, said process further comprising passing the combined by-product stream through said rearrangement reactor prior to introducing the combined by-product stream into said second distillation column.

7. The process of claim 1 wherein said second distillation column further comprises a phenol return conduit that is in fluid communication with said reaction unit, said process further comprising removing phenol from said second distillation column and introducing the removed phenol into said reaction unit by means of said phenol return conduit.

8. An apparatus for preparing purified 2,2-bis-(4-hydroxyphenyl)propane comprising in sequence:

(i) a reaction unit containing cross-linked sulfonated polystyrene resins;

(ii) a first distillation column that is downstream from and in fluid communication with said reaction unit;

(iii) a second distillation column that is downstream from and in fluid communication with said first distillation column; and (iv) a crystallization unit that is downstream from and in fluid communication with said second distillation column, said crystallization unit comprising a by-product conduit that is in fluid communication with said second distillation column.

9. The apparatus of claim 8 further comprising a rearrangement reactor filled with cross-linked sulfonated polystyrene resin, wherein said rearrangement reactor is in fluid communication with said crystallization unit and said second distillation column by means of said by-product conduit.

10. The apparatus of claim 8 further comprising a second crystallization unit that is downstream from and in fluid communication with said crystallization unit, said second crystallization unit comprising a second by-product conduit that is in fluid communication with the by-product conduit of said crystallization unit.

11. The apparatus of claim 10 further comprising a rearrangement reactor filled with cross-linked sulfonated polystyrene resin, said rearrangement reactor being in fluid communication with said crystallization unit, said second crystallization unit and said second distillation column by means of said by-product conduit and said second by-product conduit.

12. The apparatus of claim 8 wherein said second distillation column further comprises a phenol return conduit that is in fluid communication with said reaction unit.

* * * * *